US00PP17012P3

(12) United States Plant Patent
Arene-Querard

(10) Patent No.: US PP17,012 P3
(45) Date of Patent: Aug. 15, 2006

(54) ***CLEMATIS* PLANT NAMED 'CLEMINOV 51'**

(50) Latin Name: *Clematis hybrida*
Varietal Denomination: Cleminov 51

(75) Inventor: Laurence Arene-Querard, Beaucouzé (FR)

(73) Assignee: Agri Obtentions S.A., Guyancort Cedex (FR)

( * ) Notice: Subject to any disclaimer, the term of this patent is extended or adjusted under 35 U.S.C. 154(b) by 25 days.

(21) Appl. No.: 11/013,411

(22) Filed: Dec. 17, 2004

(65) Prior Publication Data

US 2006/0137053 P1 Jun. 22, 2006

(51) Int. Cl.
*A01H 5/00* (2006.01)

(52) U.S. Cl. ..... Plt./228

(58) Field of Classification Search ..... Plt./228
See application file for complete search history.

*Primary Examiner*—Kent Bell
(74) *Attorney, Agent, or Firm*—Buchanan Ingersoll PC

(57) ABSTRACT

A new and distinct variety of *Clematis* plant is provided that is the product of a controlled breeding program. Attractive purple flowers are formed on a substantially continuous basis over an extended period of time. The growth habit is compact and bushy and the plant well resists wilting and withering. The plant can be readily propagated by the use of cuttings and can be grown to advantage to provide colorful ornamentation in the landscape and in pots.

2 Drawing Sheets

Botanical/commercial classification: *Clematis hybrida*/ Clematis Plant.
Varietal denomination: cv. 'Cleminov 51'.

SUMMARY OF THE INVENTION

A new and distinct *Clematis* plant is provided that is the product of a controlled interspecific hybridization program carried out during 1994 at Beaucouzé, France. The female parent (i.e., the seed parent) was 'The President' *Clematis* variety (non-patented in the United States), and the male parent (i.e., pollen parent) was the 'Olgae' variety (non-patented in the United States). A single plant of the new variety of the present invention was selected during June 2002 primarily on the basis of the attractiveness of the flowers and the extremely long flowering season.

It was found that the new *Clematis* variety of the present invention displays the following combination of characteristics:

(a) exhibits a compact and bushy growth habit, (b) forms in abundance on a substantially continuous basis over an extended period of time attractive purple flowers, and (c) readily can be propagated by the use of cuttings.

The new variety commonly flowers on a substantially continuous basis for approximately 4 to 5 months on average from May to September which significantly exceeds the flowering period of many other *Clematis* varieties. Also, the new variety has been found to well resist the wilting and withering phenomenon commonly observed with respect to many previously known climbing *Clematis* varieties.

The new variety of the present invention well meets the needs of the horticultural industry and is particularly well suited for providing colorful ornamentation in the landscape and in pots.

The new variety of the present invention can be readily distinguished from all other *Clematis* varieties of which I am aware including its parental varieties on the basis of the above-identified combination of characteristics. More specifically, 'The President' variety is considerably less compact in its growth habit and the duration of the blooming is considerably shorter. Also, the 'Olgae' variety forms smaller flowers which are displayed for a considerably shorter period of time.

The new variety of the present invention has been found at Beaucouzé, France, to readily undergo asexual propagation by the rooting of cuttings. The distinctive combination of characteristics of the new variety is reliably transmitted to subsequent generations following such propagation. Accordingly, the new variety propagates true to type via asexual reproduction.

The new variety has been named 'Cleminov 51'.

BRIEF DESCRIPTION OF THE PHOTOGRAPH

The accompanying photographs show typical four year-old plants during the summer while growing at Beaucouzé, France. The plants had been asexually reproduced by the rooting of cuttings.

DETAILED DESCRIPTION

Figure 1:
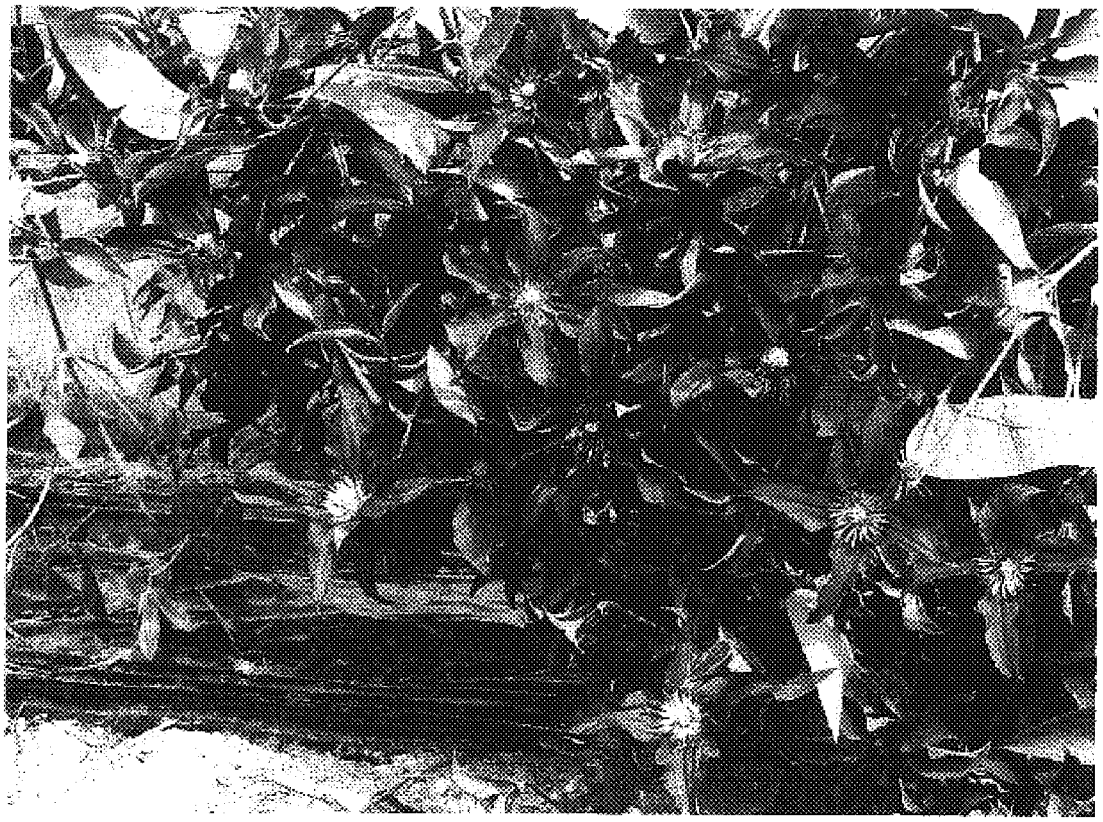
FIG. 1 shows the typical compact growth habit of the new variety with the abundant presence of attractive purple flowers and foliage while growing in the landscape.

The following description is based on the observation of five year-old plants of the new variety while growing outdoors at Beaucouzé, France during September 2004. The plants had been asexually reproduced by the rooting of cuttings. Color designations are with reference to The R.H.S. Colour Chart of The Royal Horticultural Society London, England. When employed common color terms are to be accorded their customary dictionary significance.

Origin: A product of the controlled cross of 'The President' variety (female) and the 'Olgae' variety (male).

Plant:

*Habit.*—Compact and bushy.

*Height.*—Commonly approximately 40 to 50 cm on average when grown in a pot and approximately 100 cm on average when grown in the landscape.

*Width.*—Commonly approximately 45 cm on average.

Branches:

*Color.*—Young stems: commonly near Yellow-Green Group 144A. Adult stems: commonly near Greyed-Orange Group 175C.

*Stem length.*—Up to approximately 150 cm.

*Internode length.*—Varies somewhat with age of plant, and typically is approximately 5.2 cm on average.

Foliage:

*Leaf general appearance.*—Dense with a dull aspect (non-glossy).

*Leaf length.*—Commonly approximately 6 to 6.5 cm on average.

*Leaf width.*—Commonly approximately 3 to 4 cm on average.

*Leaf shape.*—Ovate to lanceolate.

*Leaf base.*—Obtuse to attenuate.

*Leaf apex.*—Generally cuspidate to acute.

*Leaf margin.*—Entire.

*Leaf color.*—New foliage: Upper surface: near Yellow-Green Group 144A. Under surface: near Yellow-Green Group 144A. Mature foliage: Upper surface: near Green Group 143A with lighter green venation. Under surface: near Green Group 139C.

*Petioles.*—Commonly approximately 2.3 cm in length, firm, and commonly near Yellow-Green Group 144C in coloration with the coloration sometimes varying with the location of the petiole along the stem.

Inflorescence:

*Number.*—Commonly approximately 5 or 6 on average per stem.

*Time of blooming.*—Commonly from May to September.

*Duration of blooming.*—Commonly approximately 4 to 5 months on average on a substantially continuous basis.

*Peduncle.*—Commonly approximately 3 to 6 cm in length on average, approximately 0.2 cm in diameter on average, and near Brown Group 200A in coloration.

*Buds.*—Urn-shaped, medium in size, and commonly approximately 3.5 cm in length on average.

*Size.*—A fully open individual flower commonly measures approximately 10 cm in diameter on average. The flower when fully open is relatively flat and of an insignificant depth as illustrated in FIG. 1.

*Configuration.*—Disc-shaped.

*Tepal number.*—Between 4 and 6 per flower and most commonly 6.

*Tepal arrangement.*—Radial.

*Overall tepal shape.*—Elongated.

*Tepal apex.*—Pointed.

*Tepal margin.*—Entire.

*Tepal texture.*—Firm with superior resistance to wilting and withering.

Figure 2:
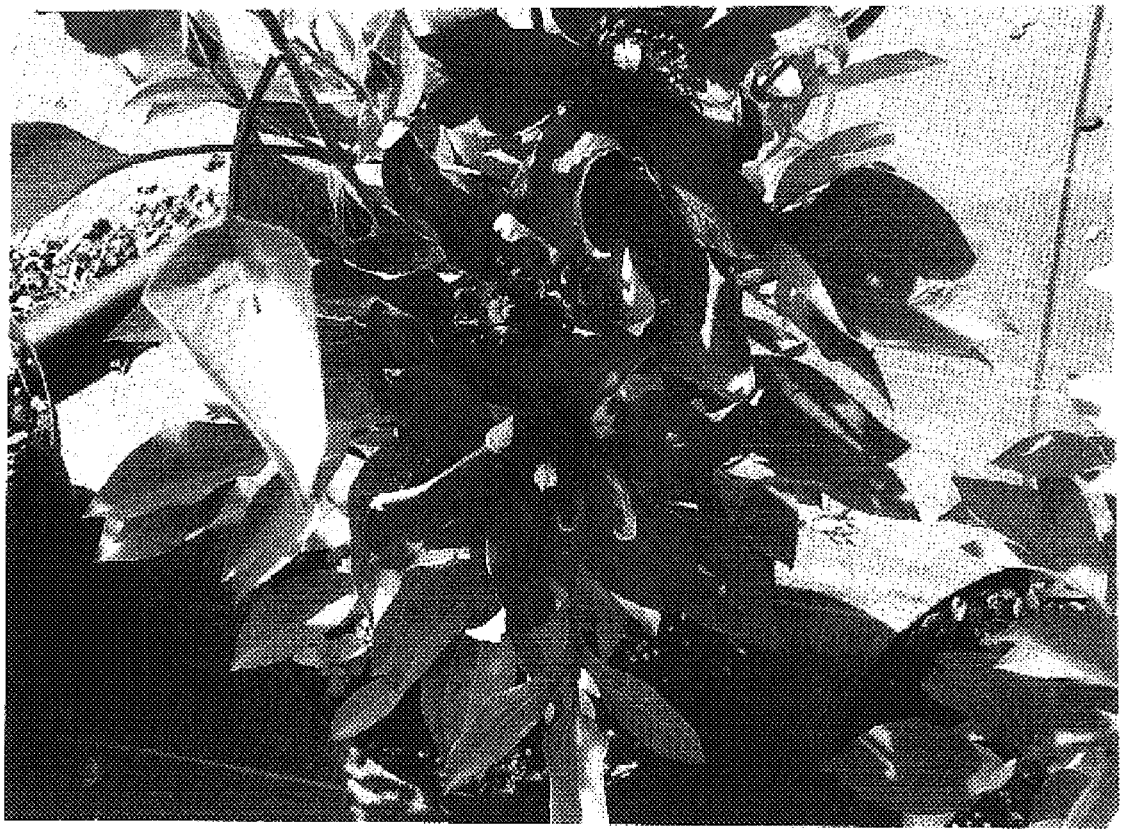
FIG. 2 shows a close view of the attractive purple flowers and foliage of the new variety while growing in a pot. The arrangement of the stamens and pistils also is shown.

*Tepal color.*—When fully open on the upper surface Violet Group 86A with darker marking towards the center as shown in FIG. 2, and on the under surface Violet-Blue Group 89C.

*Lastingness.*—A typical flower commonly lasts approximately 7 days on the plant on average.

*Fragrance.*—Very slight.

*Stamens.*—Approximately 46 on average.

*Pollen.*—Present and near Violet-Blue Group 89D in coloration.

*Anthers.*—Near Purple Group 79A in coloration, approximately 0.4 cm in length, and generally present in a ring arrangement.

*Filaments.*—Approximately 1.6 cm in length and commonly variable in coloration.

*Pistils.*—Approximately 50 on average.

*Styles.*—Near Yellow-Green Group 150D in coloration and approximately 1.3 cm in length.

*Stigmas.*—Near Yellow-Green Group 150D in coloration and approximately 1 mm in length on average.

*Hips.*—Commonly feathery in configuration, tomentose, approximately 3 cm in length, approximately 0.5 cm in width, and near Greyed-Orange Group 165A when mature.

*Seeds.*—Commonly one per hip, feathery in appearance, and near Greyed-Orange Group 16A when mature.

The disease resistance of the new cultivar during observations to date has been found to be comparable to that of *Clematis* plants in general with no particular disease or pest problems having been encountered during observations to date.

Plants of the 'Cleminov 51' variety have well withstood a temperature as low as −8° C. at Beaucouzé, France. Accordingly, considerable hardiness can be attributed to the new variety.

Plants of the new 'Cleminov 51' variety have not been observed under all possible environmental conditions to date. Accordingly, it is possible that the phenotype expression may vary somewhat with changes in light intensity and duration, cultural practices, and other environmental conditions.

What is claimed is:

1. A new and distinct *Clematis* plant that exhibits the following combination of characteristics:

(a) exhibits a compact and bushy growth habit, (b) forms in abundance on a substantially continuous basis over an extended period of time attractive purple flowers, and (c) readily can be propagated by the use of cuttings;

substantially as illustrated and described.

* * * * *